(12) United States Patent
Eckerskorn et al.

(10) Patent No.: US 7,169,278 B2
(45) Date of Patent: Jan. 30, 2007

(54) APPARATUS AND SEPARATION MEDIA FOR SEPARATING PARTICLES IN FREE-FLOW ELECTROPHORESIS

(75) Inventors: Christoph Eckerskorn, Ottobrunn (DE); Hans-Jörg Grill, Männedorf (CH); Gerhard Weber, Kirchheim (DE); Peter Weber, München (DE); David Yost, Poolesville, MD (US)

(73) Assignee: Tecan Trading AG, Mannedorf (CH)

( * ) Notice: Subject to any disclaimer, the term of this patent is extended or adjusted under 35 U.S.C. 154(b) by 453 days.

(21) Appl. No.: 10/347,108

(22) Filed: Jan. 17, 2003

(65) Prior Publication Data
US 2004/0050698 A1    Mar. 18, 2004

Related U.S. Application Data

(60) Provisional application No. 60/352,313, filed on Jan. 28, 2002.

(30) Foreign Application Priority Data
Jan. 21, 2002   (CH) ...................................... 0086/02

(51) Int. Cl.
*B01D 57/02*   (2006.01)
(52) U.S. Cl. ...................... 204/600; 204/644; 204/450
(58) Field of Classification Search ............... 204/450, 204/451, 518, 600, 644
See application file for complete search history.

(56) References Cited

U.S. PATENT DOCUMENTS

| | | | | |
|---|---|---|---|---|
| 4,465,582 A | * | 8/1984 | Richman | 204/600 |
| 5,108,568 A | * | 4/1992 | Van Alstine | 204/450 |
| 5,162,505 A | * | 11/1992 | Dean et al. | 530/391.5 |
| 5,275,706 A | * | 1/1994 | Weber | 204/450 |
| 5,284,558 A | | 2/1994 | Linhardt et al. | 204/182.8 |
| 5,298,143 A | * | 3/1994 | Ivory et al. | 204/543 |
| 5,332,480 A | * | 7/1994 | Datta et al. | 204/451 |
| 5,431,793 A | * | 7/1995 | Wang et al. | 204/452 |
| 5,459,080 A | | 10/1995 | Adamczyk et al. | 436/538 |
| 5,630,924 A | * | 5/1997 | Fuchs et al. | 204/601 |
| 5,670,381 A | | 9/1997 | Jou et al. | 436/518 |

(Continued)

FOREIGN PATENT DOCUMENTS

EP    0 103 965    3/1984

(Continued)

OTHER PUBLICATIONS

Völkl et al, *Isolation of peroxisome subpopulations from rat liver by means of immune free-flow electrophoresis*, Electrophoresis, 19, pp. 1140-1144 (1998).

*Primary Examiner*—Nam Nguyen
*Assistant Examiner*—Anthony Fick
(74) *Attorney, Agent, or Firm*—Notaro Michalos P.C.

(57) ABSTRACT

A free-flow electrophoresis (FFE) apparatus and separation medium for separating particles therefore, includes a separation chamber with a dosage pump for conveying medium, electrodes for applying an electric field in the medium and sample injection points for adding a mixture of particles to be separated and fractionation points for removing the particles. Definable charge labels couple with the particles to form charge-modified particles which display with a different migratory behavior in FFE The apparatus includes focusing buffers between the separation medium and at least one electrode which has much higher electrical conductivity than the separation medium.

19 Claims, 2 Drawing Sheets

U.S. PATENT DOCUMENTS

| | | |
|---|---|---|
| 5,674,750 A * | 10/1997 | Kraus et al. ................. 435/372 |
| 5,807,748 A * | 9/1998 | Bailey ......................... 436/89 |
| 5,948,231 A | 9/1999 | Fuchs et al. ................. 204/601 |
| 2001/0015320 A1 | 8/2001 | Anderson et al. |
| 2001/0027918 A1 | 10/2001 | Parce et al. |
| 2002/0008027 A1 * | 1/2002 | Rhodes et al. .............. 204/450 |

FOREIGN PATENT DOCUMENTS

WO     WO 01/77655     10/2001

\* cited by examiner

APPARATUS AND SEPARATION MEDIA FOR SEPARATING PARTICLES IN FREE-FLOW ELECTROPHORESIS

CROSS-REFERENCE TO RELATED APPLICATION

This application claims prior from U.S. Provisional Patent Application Ser. No. 60/352.313 filed Jan. 28, 2002, and Swiss Patent Application Serial No. 2002 0086/02 filed Jan. 28, 2002.

FIELD AND BACKGROUND OF THE INVENTION

The invention relates to an apparatus, the application or use of the apparatus and separation media for separating particles by means of a free flow electrophoresis technique in accordance with the generic part given in the independent claims.

A major difficulty in diagnostic practice and research involves precisely defined sample preparations. However, the technologies in common use today, such as centrifugation, filtration, magnetic separation and FACS (Fluorescence Activated Cell Sorting) have various disadvantages, such as restricted specificity, low throughput rates, limited purification ability or also expensive apparatus for isolating and purifying cells, organelles or biomolecules (e.g. protein complexes). The most important applications for purifying cells, organelles and biomolecules (e.g. protein complexes) are found in the fields of Biopharmacy, Biotechnology, Environmental Analysis, Food Technology and Medicine. The applied techniques are either preparative (Biopharmacy and Biotechnology) or analytic (Environmental Analysis, Food Technology and Medicine) in scope.

Free-flow electrophoresis (FFE) is one of the most promising technologies for separating all possible particles [cf. Krivanova L. & Bocek P. (1998), "Continuous free-flow electrophoresis", *Electrophoresis* 19: 1064–1074]. In the field of Proteomics FFE is the technology of choice for the defined preseparation of complex protein samples in terms of their varying pI values (degree of ionization). Using FFE, the cells are separated on the basis of the electrophoretic mobility of the cells. The corresponding principles have already been characterized in depth [cf. e.g. Bondy B., Bauer J., Seuffert I. and Weber G. (1995), "Sodium chloride in separation medium enhances cell compatibility of free-flow electrophoresis", *Electrophoresis* 16: 92–97], whereas FFE has received little recognition as most cell types differ only minimally in terms of their surface charge, making the separation of these cell types difficult. One of the first refinements was the introduction of immuno-FFE which allowed specific antibodies to be bound to specific surface epitopes of the cells to be separated, making it possible to modify the electrophoretic mobility of these cells in FFE by modifying the net charge of the cell surface [cf. e.g. Hansen E. and Hannig K. (1982), "Antigen-specific electrophoretic cell separation (ASECS): Isolation of human T and B lymphocyte subpopulations by free-flow electrophoresis after reaction with antibodies", *J. Immunol. Methods* 11, 51: 197–208].

An FFE apparatus of the same generic type is described in the international patent application PCT/EP01/14408. It concerns an electrophoresis apparatus with a separation chamber through which the separation medium flows and which is a space defined by a floor and a cover and spacers separating these two from each other. In addition, this FFE apparatus encompasses a pump for supplying the separation medium which enters the separation chamber via medium feed lines and leaves the chamber via outlets. The FFE apparatus also includes electrodes for applying an electric field within the separation medium and sample injection points for adding the mixture of particles or analytes and fractionation points for removing the particles separated by FFE in the separation medium. These separated particles can be used for analytic purposes or for further preparative processing. In order to exert an influence upon the separation medium flow profile provision can be made for two or more separate dosage pump feed lines to add medium which are connected to the separation chamber in the vicinity of the fractionation points in the vicinity of the electrodes.

The patent U.S. Pat. No. 5,948,231 discloses compositions, methods, and apparatus for performing ultrafast binding assays by capillary electrophoresis or other electroseparation techniques, such as Free Flow Electrophoresis.

SUMMARY OF THE INVENTION

The aim of the present invention is to refine the preparative and analytic isolation of particles such as cells, organelles and biomolecules (e.g. protein complexes) and similar matter and that of bioparticles or biopolymers in FFE.

The aim of the present invention is fulfilled by the free-flow electrophoresis apparatus of the present invention.

In one aspect, the aim of the present invention is fulfilled a method for separating particles, in particular for separating cells, cell constituents, organelles or biomolecules and parts or complexes thereof, employing the free-flow electrophoresis apparatus of the present invention.

In another aspect, the aim of the present invention is fulfilled a separation medium for separating particles, in particular for separating cells, cell constituents, organelles or biomolecules and parts or complexes thereof in a free-flow electrophoresis apparatus of the present invention.

Additional preferred characteristics are indicated in each of the dependent claims or derive thereof respectively.

In the context of the present invention, a particle includes for instance all particle units of mass preferably of biological origin, such as cells, viruses, cell organelles, vesicles, cell nuclei, membranes and parts or aggregates thereof; in addition, biomolecules such as lipids, proteins, DNA, RNA and glucose and complexes or aggregates of biomolecules such as lipoproteins, glycoproteins, lipo-polysaccharides etc. These particles also include organic and inorganic molecules such as pharmaceuticals, polymers and similar substances.

An apparatus in accordance with the invention for separating such particles on the basis of selectively modified surface charges, in particular for separating cells, cell constituents, organelles or biomolecules and parts or complexes thereof using free-flow electrophoresis techniques, encompasses the following advantages:

Magnetic beads are not suitable for the preparative separation of particles; moreover, only a single type of particle can be isolated at one time using magnetic beads. Magnetic bead applications can therefore be substituted by the use of FFE in accordance with the invention—if positively and negatively charged labels are employed simultaneously. The FFE in accordance with the invention allows the simultaneous isolation of at least two types of particles with maximum efficiency as the individual electrophoretic mobility of the particles is increased considerably and selectively.

Many FACS applications can be substituted by FFE applications and executed by facilities which are considerably cheaper and faster and, if required, automated.

Specifically selected, living cells can be qualitatively and quantitatively isolated and isolated on a preparative or analytic scale thanks to the specificity of the antibodies used and the separation force of FEE.

For the first time it is possible to prepare samples gently for extracting a highly-purified population of organelles.

Particle mixtures can be accurately separated on a preparative and analytic scale in relatively large quantities within a short period. One example is provided by the purification of circulating tumor cells from whole blood (tumor cells are found in whole blood at the ratio of $1:10^6$ to $1:10^8$): the white blood cells (2 ml MNC fraction from 10 ml whole blood), including the tumor cells, were separated from the red blood cells in whole blood treated with heparin using a density gradient and after appropriate marking of the tumor cells (incubation with epitope-specific antibodies with charge labels) were subjected to FFE for separation. They were added at a rate of 4–10 ml per hour. The purified tumor cells were able to be extracted in 2–8 ml volumes.

The proposed free-flow electrophoresis (FFE) apparatus allows various separation techniques to be conducted using a range of selective separation parameters.

The proposed FFE method allows not only the isolation but also the selective depletion of particles from a particle mixture, such as for instance, the depletion of abundant proteins (e.g. separating serum albumin from bodily fluids, for instance blood plasma).

The adhesion of particles to the electrodes that are separated due to their particular biological relevance and the subsequent major loss of these particles, can be successfully prevented by the use of a focusing buffer consisting of an electrically highly-conductive buffer medium.

Preferred and exemplary embodiments of the apparatus in accordance with the invention for separating particles on the basis of their selectively modified net surface charge (especially for separating cells or cell constituents, organelles or biomolecules and parts or complexes thereof using free-flow electrophoresis technique) shall be described in more detail below on the basis of schematic drawings which serve only to illustrate the invention and in no way restrict its scope. In the drawing:

BRIEF DESCRIPTION OF THE DRAWINGS

FIG. 1 shows cells to be separated such that

FIG. 3 shows cells to be separated with their respective epitopes, whereby in:

FIG. 6 shows a schematic view from above of apparatuses in accordance with the invention, whereby:

FIG. 7 shows a schematic distribution of quantities of charged cells of the same type, whereby:

DESCRIPTION OF THE PREFERRED EMBODIMENTS

Figure 1A:
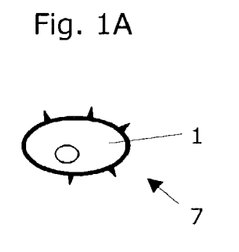
FIG. 1A have no specific epitopes.
Figure 1B:
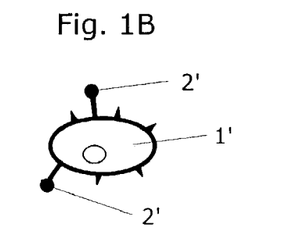
FIG. 1B have two epitopes of a first type.
Figure 1C:
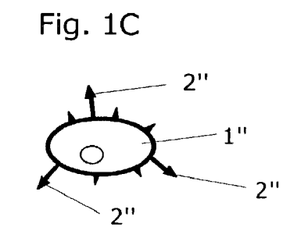
FIG. 1C have three epitopes of a second type.

FIG. 1 shows cells to be separated as an example of particles to be separated 1, 1',1". These cells do not necessarily have specific epitopes (cf. FIG. 1A). Such cells display a relatively low negative net surface charge and are very difficult to separate using FFE. However, if the cells display epitopes of a first type 2' (FIG. 1B) or of a second type 2" (FIG. 1C) these cells can be labelled epitope-specifically with charged molecules or charge labels. In general in this manner it is possible to selectively modify the net surface charge of particles by bonding charge-labelled binding molecules to these particles. This bonding can be on the basis of antigen-antibody interaction. Additional applicable interactions for modifying the net surface charge of particles in accordance with the invention for the purpose of coupling binding molecules to the particles to be separated also encompass receptor-ligand, enzyme-substrate and protein-protein interactions. Chelate formation or bonding based on general molecular interactions can also be used for this purpose, regardless of whether these are based on ionic or van der Waals forces or on hydrogen bridges. Covalent bonding can also be used for this purpose.

Using the FFE apparatus in accordance with the invention and using the FFE method in accordance with the invention it is possible to isolate the relevant cells from bodily fluids (e.g. disseminated tumor cells from blood, sputum, ascitic fluid, urine, lavages etc.) and from homogenous tissue material (e.g. solid tumors in kidney, thymus etc.) or organelles from homogenous cell material (e.g. calciosomes, coated vesicles, endosomes, endoplasmatic reticulum, Golgi cisternae, lysosomes, peroxisomes and mitochondriae) as well as proteins from proteomes or expression systems.

Figure 2:
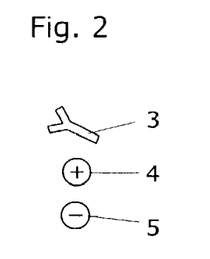
FIG. 2 shows an epitope-specific antibody and charged molecules.

FIG. 2 shows an epitope-specific antibody and two monomeric or polymeric charge labels (cf. "CL" in FIG. 5) in the form of cations 4 or anions 5. A charge label 4,5 is a molecule that is ionized at a given pH value. It can be anionic or cationic, monomeric or polymeric. Using such charge labels 4,5 it is possible to modify the net surface charge of particles in a targeted manner. Charged particles such as beads can also be used as charge labels.

Examples of anionic charge labels 5 are: Polyglutaminic acid (PGA); anionic proteins or protein derivatives such as albumin; anionic polysaccharides such as heparin or alginic acid, polyaspartic acid, polyacrylic acid and polyaminic acids with a net negative charge at an exploitable pH (e.g. in the pH range from 4 to 10). Anionic polymers with a molecular weight of 500 to approximately 500,000 Dalton are preferred. Several monomeric or polymeric charge labels can be bonded to a specific binding molecule in order to enhance the net surface charge of the particles to be separated. Examples of preferred cationic charge labels 4 include homopolymeric or copolymeric proteins with a preferred molecular weight of 500–500,000 Dalton; quaternary ammonium compositions with a nitrogen component between 1% and 10% (without counterion). Commercially available quaternary ammonium polymer compositions include e.g. the products MERQUAT.RTM (Calgon, Pittsburgh, Pa., USA), CELQUAT.RTM (National Starch and Chemical Corp., Bridgewater, N.J., USA); GAFQUAT.RTM (GAF Corp., Wayne, N.J., USA), MAGNIFLOC.RTM (CYTEC Ind., Indianapolis, Ind., USA), and Hexadimetrin-bromide (POLYBRENE.RTM) and Diethylaminoethyl-Dextran (both from Sigma Chemical Company, St. Louis, Mo., USA). These and other anionic and cationic charge labels are described in U.S. Pat. No. 5,670,381, to which explicit reference is made here and the content of which is incorporated by reference.

Such an antibody (cf. FIG. 2) shall hereinafter be termed a "binding molecule 3". The bond between a binding molecule 3 and a particle 1',1" and the bond between a charge label 4,5 and a binding molecule 3 can be covalent or non-covalent (e.g. adsorptive, based on van der Waals forces or hydrogen bridges or biotin-streptavidin interaction). The binding molecule 3 can be, for instance an antibody (cf. FIG. 2), streptavidin, biotin, a receptor, ligand, chelate generator (e.g. nickel-nitrilotriacetic acid=Ni-NTA), a low-affinity binder (protein-protein interaction) or a chemically activated molecule (e.g. activated ester, affinity label). The complex consisting of a binding molecule 3 and a charge label 4 or 5 we term a charge label binding molecule 6.

Figure 3A:
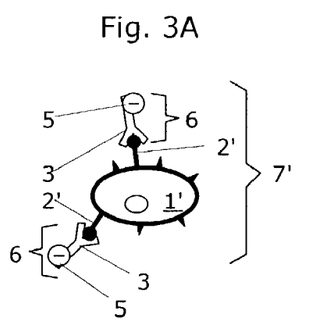
FIG. 3A both epitopes of the first type are negatively charge-labelled, making the net surface charge of the cells extremely negative, and FIG. 3B the three epitopes of the second type are positively charge-labelled, making the net surface charge of the cells extremely positive.
Figure 3B:
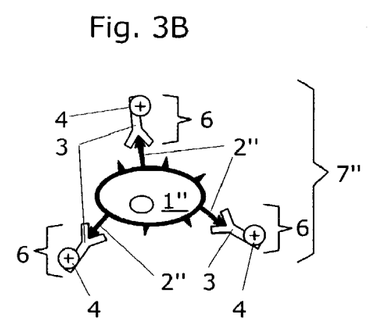
Figure 4:
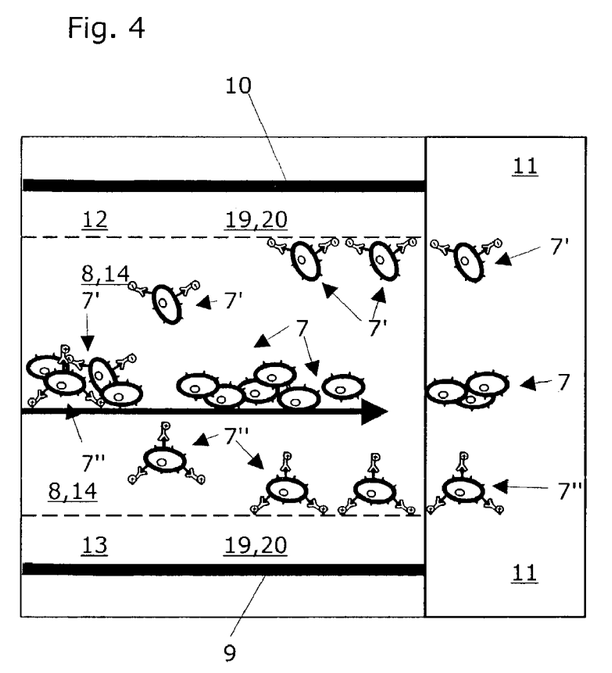
FIG. 4 shows a schematic representation of the principle of the apparatus in accordance with the invention for simultaneously separating two charge-labelled cell types.

FIG. 3 shows cells to be separated with corresponding epitopes 2',2", whereby in FIG. 3A both the epitopes of the first type 2' are negatively charge-labelled and the three epitopes of the second type in FIG. 3B are positively charge-labelled. The net surface charge of the labelled cells is modified to such a great extent in order to ensure that these cells with their specifically modified net surface charge behave differently during FFE. The complex consisting of particles 3 and the charge label binding molecule 6 is addressed as a charge modified particle 7',7". Preferably, the net surface charge of the cells is modified to such an extent that one cell type in the separation medium 8 of a device in accordance with the invention shall migrate toward the cathode 9 and the other type of cell toward the anode 10 as shown in the schematic representation of the principle in FIG. 4. In this situation the two groups of charge modified particles 7',7" or the two charge modified cell types essentially distance themselves simultaneously from the unlabelled or non-charge modified background cells 7 which are essentially moving in the middle of the separation medium 8 of the apparatus in accordance with the invention (or at least at a significant distance from the electrodes 9,10). The arrow indicates the dominant direction of flow in the separation medium 8. The various cell types which have been separated from one another are collected in a collection zone 11 and conveyed onward for further use. Collection takes place in a known manner via a series of outlets so arranged. FFE dissolution is primarily determined by the migratory behavior of the particles 7,7' and the magnitude and number of the outlets. The separation chamber 14 encompasses the chamber for the separation medium 8 and the two areas 19 adjacent to the electrodes for the focusing buffers 12,13 formed by the buffer medium 20 (cf. also FIG. 7).

Figure 7A:
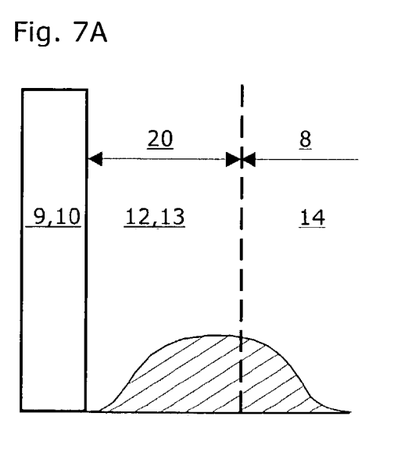
FIG. 7A shows the distribution without the use of a focusing buffer in accordance with the invention.
Figure 7B:
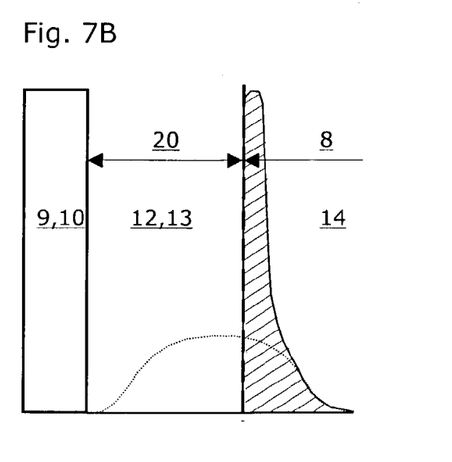
FIG. 7B shows the distribution with the use of such a focusing buffer.

The bulk of the charge modified particles 7',7" is conveyed to the outlets by FFE in a manner approximating a normal distribution if one disregards the (undesired) adhesion of charge modified particles 7',7" to the surface of the electrodes 9,10. FIG. 7A presents such a normal distribution in a schematic cross-sectional view. However, as this migratory behavior of the charge modified particles 7',7" can lead to poor FFE dissolution, in a preferred embodiment provision is made for a focusing buffer 12,13 to be located in the vicinity of each of the electrodes 9,10, whereby each buffer consists of a free-flowing separation medium displaying high electrical conductivity. By virtue of its high electrical conductivity, this focusing buffer 12,13 prevents the charge modified particles 7',7" from being able to diffuse all the way to each electrode. At the boundary between the separation medium 8 and the buffer medium 20 there is a concentration of charge modified particles 7',7" as shown in FIG. 7B. In the preferred mode, the separation medium 8 and the buffer medium 20 flow in the same direction.

Figure 5:
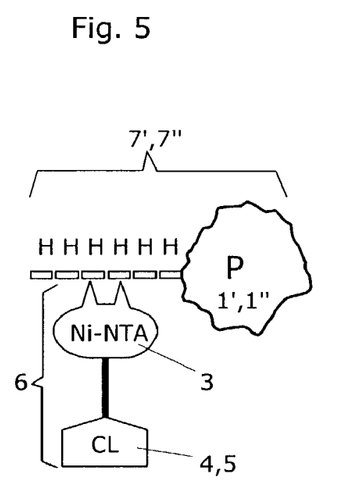
FIG. 5 shows a schematic representation of separation media used in accordance with the invention in one possible arrangement and interaction with one particle to be separated.

FIG. 5 shows a schematic representation of the separation media used in accordance with the invention in a possible arrangement and interaction with a particle to be separated. The charge modified particle 7',7" consists here of a protein P to which a chain of histidine molecules H (a so-called "His-tag") is attached in a manner known per se. Bonded to this His-tag is a charge label binding molecule 6. This charge label binding molecule 6 consists of Ni-NTA which is bonded to the histidine molecules. The anionic charge label 5 here is covalently bonded to the nickel nitrilotriacetic acid, i.e. the binding molecule 3.

FIG. 6 shows a schematic view from above of apparatus in accordance with the invention. These free-flow electrophoresis apparatus encompass at least one separation chamber 14 through which the separation medium 8 can flow. This separation chamber is defined by a floor and a cover plate and spacers holding these two apart at a distance from each other. This FFE apparatus also encompasses a dosage pump (not shown) for transporting the separation medium 8 which enters the separation chamber 14 via medium feed lines 15,15' and which exits the chamber via the outlets 16. Furthermore, the FFE apparatus encompasses two electrodes 9,10 for applying an electrical field within the separation medium 8 and sample injection points 17 for introducing a mixture of particles 7,7',7" to be separated and fractionation points 18 for removing the particles separated in the separation medium 8 by FFE. Two separate dosage pump feed lines 15' for supplying medium are connected to the separation chamber 14 in the area of the fractionation outlets in the vicinity of the electrodes 16'. These two separate dosage pump feed lines serve preferably to create a focus or guide buffer of high electrical conductivity for the charge-modified particles 7',7" in the separation medium 8 in the area 19 in the vicinity of the electrodes and are connected to a separate medium container (not shown) for the provision of buffer medium of high electrical conductivity.

The continuous isoelectric focusing (CHIEF) FFE separation technique is based on the different pI value of the particles to be separated, with this pI value being equivalent to the pH value of the surrounding, non-homogenous medium against which the particles appear neutral. FFE of particles on the basis of different isoelectric points allows analytes or particles with only minimal disparities in their pI values to be isolated. At the isoelectric point pI (i.e. at the point in the separation medium 8 displaying the pH value at which the number of negative and positive charges is equal for a given particle, e.g. a protein molecule) the total charge or net surface charge of this particle is zero. The focusing effect inherent in the separation medium 8 of a CHIEF apparatus causes a particle 1',1" which is diffused away from pI to automatically receive a (positive or negative) net surface charge and to be transported in the direction of pI again by the electrical field.

As a result of the interaction of analytes or particles with a single binding molecule with a high charge density it is to be expected that there is a major change in the pI value and therefore a rapid and total separation of the complex consisting of the particle and the binding molecule from the rest of the sample species. The continuous isoelectric focusing technique is especially suitable for the micropreparative to preparative isolation of biopolymers in general and of bioparticles, the biological function or integrity of which is certain to be within the range of the selected span of pH gradients in the separation medium. This applies in the case of many examples of viruses, bacteria, cell organelles and membrane domains, as by adding "osmotic expanders" it is possible to ensure that ideal osmotic pressure is maintained: by adding uncharged substances (e.g. glucose as a non-ionic osmotic expander) and/or salts (e.g. NaCl as an ionic osmotic expander) optimal osmotic pressure (i.e. isomolal conditions) can be achieved for a cell type (e.g. 250–310 mosmol for mammalian cells).

FIG. 6 shows an apparatus in accordance with the invention for separating charge-modified particles 7',7" from non-charge-modified particles 7 in a separating medium 8 which flows in a separation chamber 14 between two electrodes 9,10 (large arrow, 8). The separation chamber 14 encompasses the chamber for the separation medium 8 and two areas 19 adjacent to the electrodes for the guiding and focusing buffers formed by the buffer medium 20. The electrodes 9,10 are preferably embodied as electrode chambers, through which flows an electrode buffer 24 contacted by means of an electrical supply line 23,23', and which preferably has a semi-permeable membrane 25 juxtaposed with the separation chamber 14. The electrode buffer 24 is fed into the electrode chambers by means of separate feed lines 26, 26'(only partially shown in FIG. 6) and also exits this via separate outlets 27,27'. Preferably, an additional pump apparatus (not shown) is employed to circulate the electrode buffer and to cool it if required.

Figure 6A:
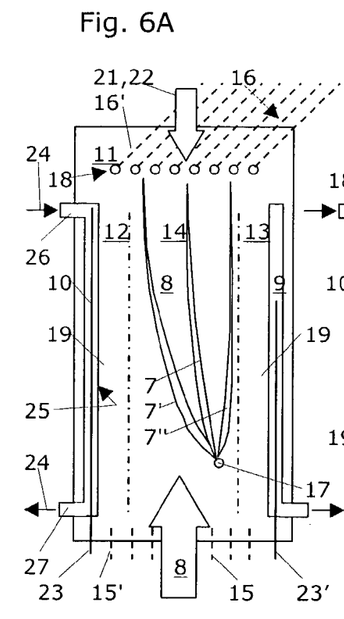
FIGS. 6A and 6D show a CHIEF device with a linear pH gradient and a homogenous field.

FIG. 6A shows such a CHIEF apparatus with a linear pH gradient. A separation medium 8 flows in a laminar manner (preferably from the bottom upwards in a tilted separation chamber) between both the electrodes (large arrow), is decelerated by the counterflow of the separation medium (small arrow) in the vicinity of the outlets, and exits the separation chamber 14 in fractions via the outlets. A sample with three groups of particles to be separated is introduced into the separation medium via the sample inlet and transported by the laminar flow of the separation medium. The three groups of particles are continuously separated, focused and collected in distinct fractions in the pH gradient resulting from the electrical field generated between the electrodes in the separation medium. As indicated in FIG. 6D, the electrical conductivity of the separation medium 8 between the two focusing buffers 12,13 for which provision is preferably made is relatively minimal and homogenous—with high electrical conductivity in the areas 19 in the vicinity of the electrodes. The pH gradient is generated in the separation medium between the two focusing buffers 12,13.

The continuous preparative zone electrophoresis (PZE) FFE separation technique is based on the difference between the electrophoretic mobility value of the particles to be separated and that of the separation medium employed. FFE zone electrophoresis makes it possible to isolate analytes and particles on the basis of differing size and/or form and/or net surface charge.

As a result of the interaction of particles with a single binding molecule with a high charge density it is to be expected that there is a major change in the electrophoretic mobility value and therefore a rapid and total separation of the complex consisting of the particle and binding molecule 3 from the rest of the sample species. The PZE FFE method is especially suitable for separating "sensitive" bioparticles and complexes when specific demands have to be placed upon the separation medium during separation. This is particularly the case when the biological function and integrity of the particles has to be maintained following separation. The special requirements in these cases are: a very restricted pH range for the separation medium, good separation medium buffer capacity, physiological compatibility of the buffer substances used, and a minimum content of various "essential" cations and anions etc. Although standard cell culture media are poorly compatible with all electrophoretic techniques, it is possible to separate cells successfully using PZE FFE.

Figure 6B:
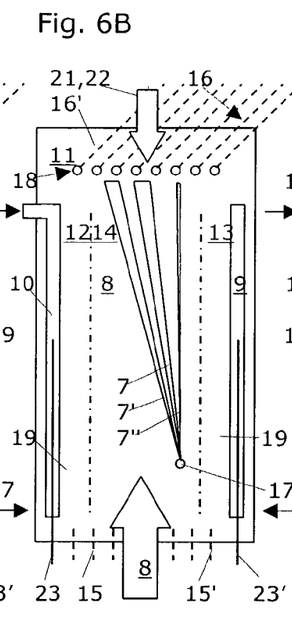
FIGS. 6B and 6E show a PZE device with a homogenous pH value and a homogenous field.

FIG. 6B shows such a PZE apparatus in which the samples are separated on the basis of their charge and to a lesser extent on the basis of their form and size. As can be seen in FIG. 6E the electrical conductivity of the separation medium 8 between the two focusing buffers 12,13 is relatively low and homogenous—with high electrical conductivity in the areas 19 in the vicinity of the electrodes. The pH value is the same throughout the entire separation medium.

The continuous isotachophoresis (CITP) FFE separation technique is also based upon the difference in the electrophoretic mobility value of the particles to be separated. In contrast to PZE FFE, separation is achieved in non-homogenous separation media and offers better dissolution due to the inherent "focusing effect": When single particles are diffused from a separated band of particles (e.g. proteins) during CITP these particles enter a medium with varying electrical field strength, resulting in the particles being accelerated or decelerated. The inherent focusing effect means that the slower or faster moving particles find their way into the dominant fraction again.

This FFE separation technique is in principle suitable for bioparticles and cells, the separation of which is not possible in a medium without special "essential cations" (e.g. $Mg^{++}$ or $Ca^{++}$) or "essential anions" (e.g. $Cl^-$) which are critical for cell stability and vitality.

Figure 6C:
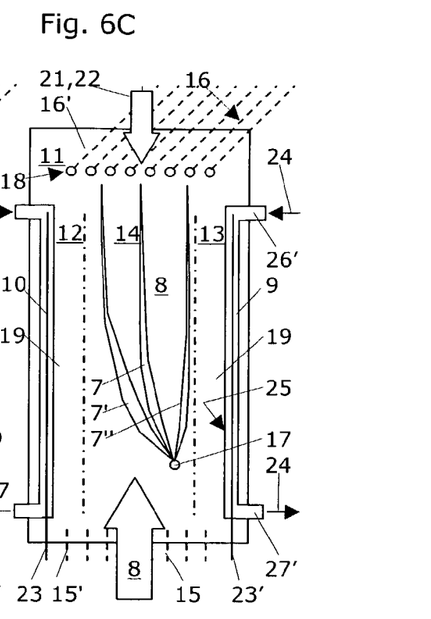
FIGS. 6C and 6F show a CITP device with a pH gradient and a field gradient.
Figure 6D:
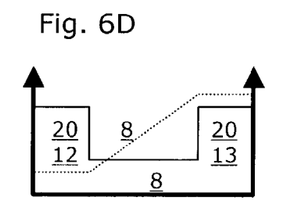
Figure 6E:
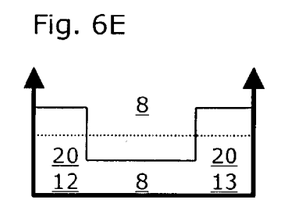
Figure 6F:
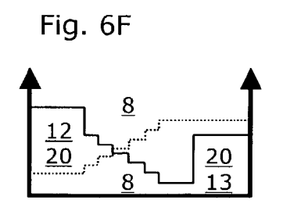

FIG. 6C shows such a CITP apparatus in which discrete spacers are used. Such discrete spacers are ions with well-known, specified mobility and which force their way between particles to be separated during CITP, contributing to efficient separation. Ampholytes can also be used as such discrete spacers. As can be seen in FIG. 6F, the electrical conductivity of the separation medium 8 between the two focusing buffers 12,13 exhibits at least a partial gradient and is non-homogenous—with high electrical conductivity in the areas 19 in the vicinity of the electrodes. Additionally, at least a partial pH gradient is formed in the separation medium 8 between both the focusing buffers 12,13, whereby the ranges of both gradients are essentially overlapping and not only the pH values, but also the electrical conductivity in the area of the focusing buffers 12,13 are different for each.

Various combinations of these separation techniques (CHIEF and PZE FFE or CHIEF and CITP) are possible. In this way for instance, it is possible to use different separation media at the same time in the separation chamber of the FFE apparatus, employing different separation parameters simultaneously.

The apparatus proposed in accordance with the invention and the method proposed in accordance with the invention allows for continuous modes of operation to be employed, whereby the particles 7,7',7" are separated employing the continuous flow of the separation medium, the uninterrupted application of the electrical field during the entire separation process, and continuous collection. In doing so, a distinction is made between the continual preparative mode (sample is introduced continuously under constant separation conditions) and semi-preparative/analytical modes (sample is introduced at intervals under constant separation conditions).

In the case of another possible non-continuous mode of operation the separation medium 8 flows continuously: The sample is injected with the high-voltage power switched off; after the sample has been introduced the transportation of medium is switched off or throttled considerably or reduced. The high-voltage current is then switched on until the sample has been separated. After a pre-determined period of time the voltage is switched off and the separated sample is eluted from the separation chamber by increasing the flow of medium and collected. Provision can also be made for an auxiliary medium 21 to be introduced into the separation chamber 14 via auxiliary medium feed lines 22 (preferably at the end of the FFE apparatus directly opposite the medium feed lines 15,15') and extracted together with the separation medium 8 via the fractionation points 18 (cf. FIGS. 6A to 6C).

FIG. 7 shows the effect of the focusing buffers 12,13, whereby the boundary between the focusing buffer with the electrically highly-conductive buffer medium 20 which virtually runs parallel to the electrode 9,10 is indicated by the broken lines. If no focusing buffer is generated (FIG. 7A) the result is an approximate normal distribution (hatched) of the particles separated from the rest of the sample on the basis of the selectively modified net surface charge. It is also possible that particles attach themselves vigorously to the electrode 9,10 (not shown) so that at times there is a significant loss of these separated particles which may be of particular biological relevance. This can be prevented successfully by means of a focusing buffer 12,13 consisting of an electrically highly-conductive buffer medium 20 (cf. FIG. 7B). By virtue of its significant electrical conductivity, the focusing buffer 12,13 behaves like an electrode 9,10, whereby particles are prevented from reaching the actual electrode 9,10 due to the high electrical conductivity of the buffer medium 20. As FIG. 7B shows, the isolated particles (hatched) concentrate at the buffer boundary in a manner which far exceeds the magnitude of the normal distribution (broken line). This means that a substantially larger number of particles at a higher concentration can be extracted from the FFE apparatus via the fractionation point 18 located in this area and made available for further use. The use of such a focusing buffer 12,13 constitutes a major improvement particularly for isolating cells, organelles, membrane fractions or biomolecular complexes which have to be separated from the rest of a sample using FFE on the basis of their selectively modified net surface charge. Conversely, it appears that the use of a focusing buffer for the fine separation of biomolecules with identical subunits and complexes thereof is less advantageous. The guide or focusing buffers 12,13 are thus formed by a buffer 20 which has far greater electrical conductivity than the separation medium 8. As electrophoretic separation performance depends upon the field strength and behaves in an inversely proportional manner with respect to the conductivity, electrophoretic separation performance within the focusing buffers 12,13 drops so dramatically that the charge-modified particles 7',7" are focused at the boundary between the separation medium 8 and the focusing buffers 12,13.

Three embodiments of immuno-FFE are presented as examples below:

EXAMPLE A

Purification of Circulating Tumor Cells from Whole Blood

A summary of the valency of disseminated tumor cells can be found in: Bockmann B, Grill H J, Giesing M. Molecular characterization of minimal residual cancer cells in patients with solid tumors. *Biomol. Eng.* 2001; 17: 95–111.

The membrane protein epithelial glycoprotein (EGP) which is specific to epithelial cells is used as a cellular surface marker. This EGP is also expressed from epithelial tumor cells (Moldenhauer G, Momburg F, Möller P, Schwartz R, Hämmerling G J. Epithelium-specific surface glycoprotein of Mr 34,000 is a widely distributed carcinoma marker. *Br J Cancer* 1987;56:714–21). The literature provides good descriptions of monoclonal antibodies with the designation Ber-EP4 which act against EGP cell surface epitopes (Latza U, Niedobitek G, Schwarting R, Nekarda H, Stein H. "Ber-EP4: new monoclonal antibody which distinguishes epithelia from mesothelia", *J Clin Pathol* 1990;43: 213–219).

This monoclonal antibody is modified for immuno-FFE in two ways:

A) A charge label 4,5 is bound directly and covalently to the antibody (the binding molecule 3).

B) Streptavidin is covalently bound to the antiserum. Biotinylated charge labels 4,5 can then be selected as required for bonding to the streptavidin.

In order to isolate circulating tumor cells, citrate or heparin whole blood from patients with, for instance mammary, ovarian or colon carcinoma is used either directly or prepared as follows:

1. White blood cells (mononuclear cells, MNC) are isolated across a density gradient using known methods.

2. Introduction of antibodies modified accordingly with charge labels 4,5.

3. Incubation employing known methods.

4. Cells separated using Immuno-FFE:

A first experiment employed the separation conditions and separation medium known from Bondy B., Bauer J., Seuffert I. and Weber G. (1995)

"Sodium chloride in the separation medium enhances cell compatibility of Free Flow Electrophoresis", *Electrophoresis* 16: 92–97. Express reference is made to this publication here and the content of which is incorporated by reference.

A second experiment employed a separation medium as described in the international application PCT/EP01/10036. Express reference is made to this publication here and the content of which is incorporated by reference.

EXAMPLE B

Isolation of Peroxisomes

Peroxisomes are cell organelles which engage in oxidative reactions with molecular oxygen. They generate peroxide oxygen for oxidative purposes.

Highly enriched peroxisomes can be isolated, for instance from rat liver using a complex density gradient centrifuge according to the method reported by Lüers et al. (Lüers G H, Hartig R, Mohr H, Hausmann M, Fahimi H D, Cremer C, Völkl A. "Immuno-isolation of highly purified peroxisomes using magnetic beads and continuous immunomagnetic sorting", *Electrophoresis* 1998;19: 1205–1210):

1. Homogenization of rat liver using known methods.
2. Centrifugation of homogenized material at 1,900×g to remove cell nuclei, cell debris, mitochondria and cells which are still intact.
3. Centrifugation of the remaining material at 25,000×g.
4. The resulting pellet contains the so-called "light microsomal fraction" (incl. peroxisomes, microsomes and some mitochondria with lysosomes), thereby constituting a mixture which also encompasses the peroxisomes.

A method already exists for enriching peroxisomes using a modified form of immuno-FFE (Voelkl A, Mohr H, Weber G, Fahimi H D. "Isolation of peroxisomes subpopulations from rat liver by means of immune free-flow electrophoresis", *Electrophoresis* 1998;19: 1140–1144. However, this known method for enriching peroxisomes using immuno-FFE is modified by the introduction of charge labels 4,5 as follows:

1. Homogenization of rat liver as known.
2. Centrifugation at 400×g to remove cell nuclei, cell debris and cells which are still intact.
3. The remaining supernatant material is then incubated with an antibody modified with charge labels 4,5 to a peroxisome membrane protein (e.g. PMP70; 70 kDa cytoplasmatic membrane protein from peroxisomes, antibodies to the C-terminal, cytoplasmatic end 11 amino acids in length).
4. Separation was conducted using immuno-FFE as described by A. Voelkl, H. Mohr, G Weber, H. D. Fahimi (*Electrophoresis* 1998, 19, 1140–1144) at a separation medium temperature of 4° C. and at a pH of 8.0 in an electrical field of 1,000 V and 100 mA and a separation medium flow velocity of approximately 5 ml/fraction per hour. The samples were introduced at approximately 2 ml/hour into the separation chamber and the separated fractions were collected using a 96-channel peristaltic pump. Each individual separation experiment lasted approximately 60–90 minutes.

EXAMPLE C

Isolation of Recombined Proteins

For the expression of recombinant proteins there are vectors which can attach a chain of 5–10 histidines onto the protein to be expressed at the 5' or 3' end of a structure (His-tags, cf. FIG. 5). These additional histidines are used for later purification of the expressed proteins. Other vectors contain, for instance glutathione S-transferase as an additional element. These vectors are suitable for the expression of recombinant proteins, e.g. in *E. coli*, Baculovirus-infected bacteria and mammalian cells. The corresponding methods for producing recombinant proteins are known to those skilled in the art.

The currently available options for purifying recombinant expressed proteins are based primarily on affinity chromatography methods. These methods are relatively easy to use and scalable, depending on the quantity of the proteins to be purified. However, affinity chromatography purification of recombinant proteins has several significant disadvantages:

1. Affinity matrix bleeding
2. Column blockage resulting from sample matrix (cellular lysate)
3. Non-specific binding of proteins
4. Enzymatic lysis of proteins (proteolysis)

The purification of recombinant proteins with poly-His-tags by means of immobilized Ni-NTA (Nickel Nitrilotriacetic Acid) chelates is known to those skilled in the art. This solid phase can be packed into chromatography columns for preparative purification (e.g. Ni-NTA agarose) and magnetic particles are available for analytic applications (e.g. Ni-NTA).

Immuno-FFE as shown in FIG. 5 in accordance with the invention is especially suitable for purifying recombinant proteins and encompasses the following steps:

1. Cellular lysis (e.g. yeasts, bacteria, mammalian cells) using the known method.
2. Bonding of charge labels 4,5 to the His-tagged proteins:
   Variation 1: Bonding of charge labels 4,5 to a binding molecule 3 in the form of Ni-NTA and bonding of this charge label binding molecule 6 to the His-tags; or
   Variation 2: Bonding of charge labels 4,5 to a binding molecule 3 in the form of an anti-poly-His antibody and bonding of the charge label binding molecule 6 to the His-tags.
3. Incubation using the known method.
4. Separation by means of FFE (qualitative but quantitative also possible):
   A first experiment employed the separation conditions and separation medium disclosed by Bondy B., Bauer J., Seuffert I. and Weber G. (1995) "Sodium chloride in the separation medium enhances cell compatibility of Free-flow Electrophoresis", *Electrophoresis* 16: 92–97. Express reference is made to this publication here and the content of which is incorporated by reference.
   A second experiment employed a separation medium as described in the international application PCT/EP01/10036. Express reference is made to this publication here and the content of which is incorporated by reference.
5. Collection of isolated His-tagged proteins
   The His-tagged proteins can be either used directly or the His-tags can be cleaved enzymatically prior to further application.

There are several options for cleaving the His-tags from the proteins:

For Variation 1:
a) Detachment of the chelate by means of known incubation with imidazole and if required, repurification of the protein in FFE;
b) Known enzymatic cleaving of His-tag with thrombin or exoprotease and if required, repurification of isolated protein in FFE.

For Variation 2:
c) Detachment of the antibody by means of known methods, e.g. by modifying the saline concentration or the pH.
d) Enzymatic cleaving of the His-tags by means of known methods.
e) Repurification with FFE.

The charge label or the agent (e.g. biomolecule) bearing the charge label can also be additionally labelled (e.g. using a dye). This enables detection during or following FFE. Charge labels can also be any type of particle (e.g. beads of all kinds, such as latex, agarose particles, colloids, etc.). Charge labels can also be practically any combination of beads and/or antibodies and/or charged molecules and/or fluorescent markers and/or stains. Beads can for instance be stained with fluorescent or other dyes. Beads can simultaneously carry fluorescent marking (internal or external), the charge label, and the binding molecule (e.g. antibody or Ni-NTA). If beads are used which have a bridge which can be cleaved enzymatically, the beads can be cleaved from the purified molecule after purification (e.g. purification of recombinant proteins with Ni-NTA). Particular preference is given to beads which are fluorescent and have charge labels and binding molecules on their surface.

TABLE 1 below indicates possible measures which can be taken to maintain the biological activity and vitality of bioparticles for the various FFE techniques:

| Measure | PZE | CITP | CHIEF |
|---|---|---|---|
| Use of media within physiological pH range | +++ | ++ | – |
| Use of non-ionic expanders | +++ | +++ | +++ |
| Use of ionic expanders | +++ | ++ | – |
| Use of "essential cations" | +++ | ++ | – |
| Use of "essential anions" | +++ | + | – |
| Separation within ideal temperature range | +++ | +++ | +++ |
| Rapid "stabilization" of bioparticles after FFE separation | +++ | +++ | +++ |

Explanation:
PZE: continuous free-flow preparative zone electrophoresis
CITP: continuous free-flow isotachophoresis
CHIEF: continuous isoelectric focusing
+++ = unrestricted use
++ = minimally restricted use
+ = can only be used in special cases
– = cannot be used The separation of particles in accordance with the invention allows concentrations of biologically relevant particles to be collected and enriched, the analysis or use of which in diagnostic or therapeutic procedures has not previously been possible due to the constraints imposed by the background of simultaneously present, related, but irrelevant particles. The FFE methods and apparatus disclosed allow the isolation and as a consequence the use of natural yet minimal concentrations of existing particles and the preparation of their biologically relevant information for use in diagnostic or therapeutic procedures. Furthermore, the isolated particles can serve to detect and characterize targets for developing medications and for targets for diagnostic, treatment selection and treatment monitoring applications not only for humans, but also for animals and plants.

Applications for the results which are achieved include, for instance, isolated tumor cells from whole blood for identifying targets in developing medications against migratory tumor cells.

Identical reference symbols are used for the same features in all figures even if they are not expressly cited as such.

The methods in accordance with the invention made known are also suitable (with appropriate modifications if required) for use in the various areas of chromatography, such as affinity chromatography of organic or inorganic molecules and polymers.

The invention claimed is:

1. A free-flow electrophoresis (FFE) apparatus for separating particles with a separation chamber adapted for the flow-through of a separation medium and defined by a floor, a cover and spacers to maintain the floor and the cover at a distance from each other, the FFE apparatus further comprising:
   (a) a dosage pump for conveying a separation medium that enters the separation chamber by way of medium feed lines and that leaves said separation chamber by way of outlets;
   (b) an anode and a cathode located at a distance from each other for applying an electric field in the separation medium that flows between these two electrodes;
   (c) sample injection points for adding a mixture of particles to be separated in the separation medium;
   (d) fractionation points for removing the particles in the separation medium that have been separated by FFE; and
   (e) selectively defined charge labels for coupling with particles to be separated and for generating charge-modified particles that have a different migratory behavior in FFE due to their selectively modified net surface charge than non-charge-modified particles;
   wherein the FFE apparatus further comprises two focusing areas arranged in the vicinity of the anode or cathode and between the separation medium and these two electrodes, whereby said focusing areas consist of a focusing buffer that is fed to the focusing areas via separate feed lines, the focusing buffer flowing in the same direction like the separation medium, but having much higher electrical conductivity than the separation medium such that a fluidic boundary is created between the separation medium and the focusing buffer in an area between the anode and cathode, whereby charge-modified particles are focused within the separation medium and close to these fluidic boundaries at the border of the focusing areas.

2. The FFE apparatus in accordance with claim 1, wherein a more rapid first flow is created in the focusing buffer within the focusing areas in the vicinity of the anode and the cathode of the apparatus, than in the separation medium.

3. The FFE apparatus in accordance with claim 1, wherein the strength of the electrical field generated by the FFE apparatus during its operation is adjustable to match a selectively modified net surface charge of the particles to be separated.

4. The FFE apparatus in accordance with claim 1, including separation media that adjust the net surface charge of the particles to be separated such that they match the strength of the electrical field generated by this apparatus.

5. The FFE apparatus in accordance with claim 1, including separation media that modify the net surface charge of the particles so that a first fraction of these particles travels essentially simultaneously and selectively toward the cathode of the apparatus and a second fraction towards the anode of the apparatus.

6. The FFE apparatus in accordance with claim 4, wherein the separation media encompass charge labels which are bound to binding molecules and which have a strong positive or negative charge.

7. The FFE apparatus in accordance with claim 6, wherein the charge labels are covalently bound to the binding molecules.

8. The FFE apparatus in accordance with claim 1, wherein the dosage pump encompasses additional feed lines or the FFE apparatus encompasses a further dosage pump for conveying an auxiliary medium which enters the separation chamber via auxiliary medium feed lines and then leaves said chamber via fractionation points and outlets.

9. The FFE apparatus in accordance with claim 8, wherein a decelerating counter flow to the separation medium is produced by the auxiliary medium.

10. The FFE apparatus in accordance with claim 1, wherein the cathode and anode are embodied as electrode chambers which are flown through by an electrode buffer that is contacted to an electrical supply line.

11. A separation medium for separating particles in a free-flow electrophoresis (FFE) apparatus with at least one separation chamber, adapted for flow-through of a separation medium and defined by a floor, a cover and spacers to maintain the floor and cover at a distance from each other, the FFE apparatus also comprising:
   a) a dosage pump for conveying a separation medium that enters the separation chamber by way of medium feed lines and that leaves said separation chamber by way of outlets;
   b) an anode and a cathode located at a distance from each other for applying an electric field in the separation medium that flows between these two electrodes;
   c) sample injection points for adding a mixture of particles to be separated in the separation medium; and
   d) fractionation points for removing the particles in the separation medium that have been separated by FFE;
   e) individually selectable charge labels for combining with the particles to be separated and for generating charge-modified particles that have a different migratory behavior than non-charge modified particles in FFE due to their selectively modified net surface charge;
   wherein the separation medium embodies an electrically highly-conductive focusing buffer, which has much higher electrical conductivity than the separation medium, and which is introduced into focusing areas of the FFE apparatus in the vicinity of the electrodes via separate feed lines in order to create two electrically highly-conductive focusing areas for the charge-modified particles between the electrodes and the separation medium such that a fluidic boundary is created between the separation medium and the focusing buffer in an area between to the anode and cathode, whereby charge-modified particles are focused within the separation medium and close to these fluidic boundaries at the border of the focusing areas.

12. The separation medium in accordance with claim 11, further comprising is a charge label binding molecule with which the net surface charge of the particles is modified so that a first fraction of these particles travels essentially simultaneously and selectively toward the cathode and a second fraction towards the anode of the apparatus.

13. The separation medium in accordance with claim 12, wherein the charge label binding molecule encompasses a binding molecule and a charge label with a strong positive or negative charge.

14. The separation medium in accordance with claim 13, wherein the charge label is selected from the group comprising: a bead, latex or agarose particle, and a molecule, and wherein the charge label is bound to the binding molecule.

15. The separation medium in accordance with claim 13, wherein the binding molecule is an epitope-specific antibody or a Ni-NTA molecule, which is immobilized on the particle surfaces.

16. The separation medium in accordance with claim 13, wherein the charge label is covalently bound to the binding molecule.

17. The separation medium in accordance with claim 13, wherein the binding molecule is selected from a group encompassing neutravidin, streptavidin/biotin, secondary antibody systems, and chelate generators.

18. The separation medium in accordance with claim 12, wherein the charge label binding molecule or the binding molecule encompasses a detectable label selected form the group comprising: a dye and a fluorescent material, for detecting the current position of charge-modified particles in the separation medium.

19. The separation medium in accordance with claim 12, wherein the charge label binding molecule encompasses one or several charge labels or polymers thereof selected from a group encompassing lysine, arginine, histidine, aspartate and glutamate.

* * * * *